(12) United States Patent
Smith

(10) Patent No.: US 6,269,142 B1
(45) Date of Patent: Jul. 31, 2001

(54) INTERRUPTED-FAN-BEAM IMAGING

(76) Inventor: Steven W. Smith, 16129 Bennye Lee Dr., Poway, CA (US) 92064

(*) Notice: Subject to any disclaimer, the term of this patent is extended or adjusted under 35 U.S.C. 154(b) by 0 days.

(21) Appl. No.: 09/371,816

(22) Filed: Aug. 11, 1999

(51) Int. Cl.[7] .................................................. G01N 23/10
(52) U.S. Cl. ........................... 378/57; 378/87; 378/160
(58) Field of Search ............................. 378/57, 86, 87, 378/88, 89, 62, 160; 250/505.1, 350, 351

(56) References Cited

U.S. PATENT DOCUMENTS

| | | | |
|---|---|---|---|
| Re. 28,544 | 9/1975 | Stein et al. | 378/146 |
| 4,799,247 | 1/1989 | Annis et al. | 378/87 |
| 4,864,142 | 9/1989 | Gomberg | 250/390.04 |
| 4,974,247 | 11/1990 | Friddell | 378/90 |
| 5,022,062 | 6/1991 | Annis | 378/86 |
| 5,181,234 | 1/1993 | Smith | 378/87 |
| 5,195,121 * | 3/1993 | Charrier | 378/160 |
| 6,034,371 * | 3/2000 | Kormos et al. | 378/160 |
| 6,094,472 * | 7/2000 | Smith | 378/86 |

* cited by examiner

*Primary Examiner*—Robert H. Kim
*Assistant Examiner*—Drew A Dunn
(74) *Attorney, Agent, or Firm*—Brown, Martin, Haller, McClain

(57) ABSTRACT

Interrupted-Fan-Beam imaging is a method of producing back-scatter x-ray images from conventional line scan systems, such as those used for luggage and cargo inspection. Since back-scatter and transmission images are formed from different physical principles, the use of both images provides a more thorough security inspection. A mathematical relation relates the signal-to-noise ratio to the spatial resolution in an Interrupted-Fan-Beam image. When used in conjunction with typical operating values of x-ray systems, such as flux level and number of pixels, this relation provides the performance level of the Interrupted-Fan-Beam technique.

19 Claims, 5 Drawing Sheets

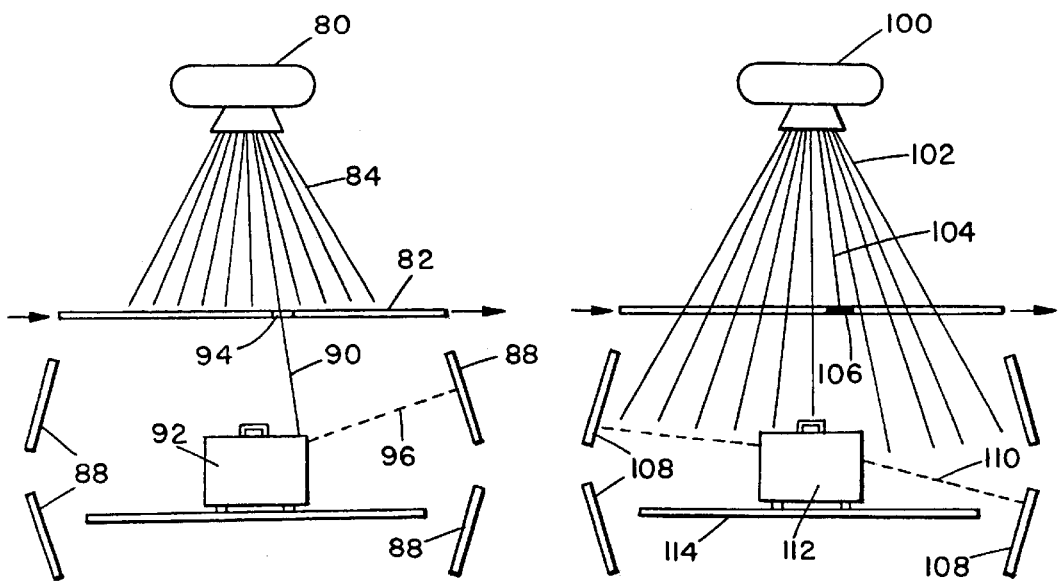
FIG. 4a
PRIOR ART
FIG. 5a
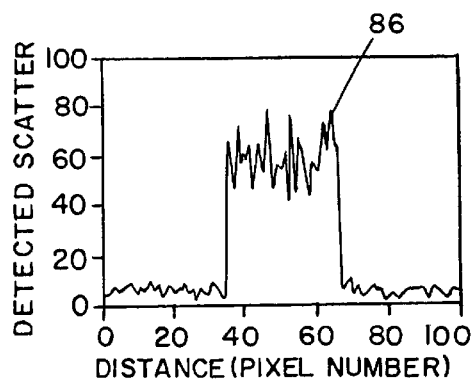
FIG 4b
PRIOR ART
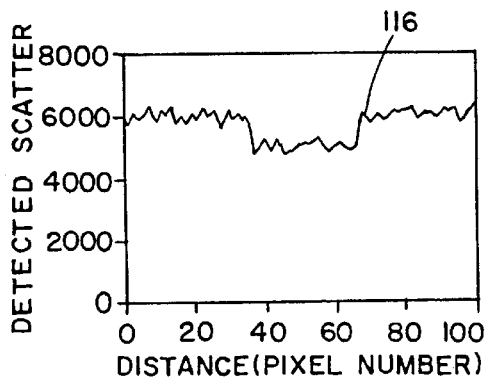
FIG. 5b

INTERRUPTED-FAN-BEAM IMAGING

BACKGROUND OF THE INVENTION

The specification herein incorporates disclosure contained in Disclosure Document No. 433067 which was received in the U.S.P.T.O. on Feb. 25, 1998.

The security inspection of luggage and other containers commonly utilizes two types of x-ray imaging systems generally referred to as the "line scan" and the "flying spot" systems. A line scan system employs an x-ray source and slit collimator to form a fan beam of x-rays directed perpendicular to the conveyor belt. As an inspected item intersects the fan beam, x-rays pass through the item to a multi-element linear array detector positioned below the inspected item in line with the fan beam. Inspected items are most often moved through the fan beam utilizing a moving inspection surface, such as a conveyor belt, with the multi-element detector located below the inspection surface. The array detector collects the transmitted x-rays for processing into transmission x-ray images of the inspected item.

A key feature of the line scan geometry is the use of the multi-element detector to obtain spatial resolution along the scan line. The detectors of some line scan systems are designed to provide separate signals for the low-energy and the high-energy x-rays. The separate signals are used to create separate images of the low and high-energy attenuation properties of the inspected objects. For example, a line scan system having a configuration including both low-energy and high-energy x-rays may be used to discriminate between organic and inorganic materials.

The second common imaging system, the flying spot system, also utilizes an x-ray source having a slit collimator to form a fan beam as in the above described line scan system. However, in the flying spot system, the fan beam is additionally collimated by a second rotating chopper that is positioned in the path of the fan beam between the x-ray source and the target item to be scanned As the chopper rotates, slits in the second chopper permit a pencil beam of x-rays to sweep rapidly across the target item.

The transmission x-ray detector in the flying-spot x-ray system produces a single signal related to the total number of x-rays striking anywhere along its length. Thus, the spatial resolution along the scan line is determined by the controlled movement of the pencil beam of x-rays produced as a result of the instantaneous positioning of the chopper as it rotates. Each pixel in an acquired image corresponds to a small area on the conveyer belt or inspected item that is illuminated by a pencil beam of x-rays. For example, an image composed of 800 pixels along a scan line corresponds to a pencil beam having a nominal width of 1/800th of the scan line length.

A significant advantage of the flying spot system over the line scan system is that it can be used to acquire back-scatter x-ray images and forward-scatter x-ray images which more readily detect materials having low atomic numbers, also referred to as "low Z" materials. Back-scatter and forward-scatter x-rays, collectively referred to as "back-scatter" x-rays, are scattered or reflected from an inspected object, and thus, move in random directions. In contrast, transmitted x-rays are transmitted or partially transmitted through the object being inspected and are focused upon the transmission detectors. The back-scatter detectors utilized by the flying spot system are large area x-ray collectors that do not rely on spatial resolution to form an image. Thus, the random movements of the scattered or reflected x-rays do not present a problem for the flying spot system. In comparison, line scan systems, which utilize transmission detectors that inherently rely on the x-rays being focused to form an image, are unable to acquire back-scatter images.

The advantage of the line scan system over the flying spot system is the more efficient use of x-ray flux. The flying spot system, which employs a rotating chopper, only uses a small fraction of the x-rays present in the fan beam. In contrast, the line scan system utilizes the entire fan beam to produce an image. Because the signal-to-noise ratio (SNR) of an x-ray image is determined by the number of x-rays that are used to create the image, flying spot systems do not provide high quality images. A common approach to improving image quality is to increase the power of the x-ray source to compensate for the inefficient x-ray flux usage. For example, rotating-anode x-ray tubes, special electrical wiring to power the system, and better heat dissipation configurations may be utilized to increase x-ray power. However, these methods produce disadvantages in both cost and complexity.

SUMMARY OF THE INVENTION

It is an advantage of the present invention to scan an object using both back-scatter imaging and line scan geometry.

It is another advantage of the present invention to provide x-ray imaging that reduces operational costs through efficient flux utilization.

It is a further advantage of the present invention to provide a more thorough security inspection system and method of inspection through the use of both back-scatter and transmission images.

In an exemplary embodiment, the Interrupted-Fan-Beam system produces both transmission images and back scatter images of target items. The Interrupted-Fan-Beam system includes an x-ray source and a slit collimator that together produce a fan beam of x-rays directed along a scan line toward a target object. As a conveyor belt moves the target object through the fan beam, consecutive portions of the object intersect the fan beam along the scan line, and images of the portions of the object are produced from the transmission and backscatter signals.

The x-rays that strike the object are transmitted through the object, absorbed by the object, and/or scattered by the object. The x-rays that are transmitted through the target object are collected by the transmission x-ray detector located on the opposite side of the object from the x-ray source, along the scan line. The x-rays that are absorbed create a dark area in the transmission image to indicate the presence of high atomic weight material in the target object.

Scatter detectors collect x-rays that are scattered from the object along the entire fan beam. To establish spatial resolution along the scan line in the back-scatter signal, and to define pixel size, portions of the fan beam are consecutively blocked utilizing a rotating beam-stop that is positioned between the target object and the x-ray source. The beam-stop is designed to have at least one radial member that projects outward from a central axis, such that as the axis of the beam-stop rotates, the radial member passes through the fan beam. In the exemplary embodiment, the width of the blocked x-rays defines the pixel size. The resulting back-scatter signal shows a decrease where the void in the fan beam sweeps across the target object.

The Interrupted-Fan-Beam system produces both transmission signals and back-scatter signals of the intersected portions of the object. These signals may be displayed separately as transmission and back-scatter images representative of the intersected portions of the target objects In one embodiment, the back-scatter signal is calibrated and combined with the transmission signal to produce a high resolution, low noise combination image.

BRIEF DESCRIPTION OF THE DRAWINGS

The present invention will be better understood from the following detailed description of a preferred embodiment of the invention, taken in conjunction with the accompanying drawings in which like reference numerals refer to like parts and in which:

FIG. 4a is a side view of flying spot system of the prior art imaging an object;

FIG. 4b illustrates the resulting detector signal of the flying spot image of FIG. 4a;

FIG. 5a is a side view of the IFB imaging system imaging an object;

FIG. 5b illustrates the resulting detector signal of the IFB image of FIG. 5a;

DETAILED DESCRIPTION OF THE PREFERRED EMBODIMENTS

Figure 1:
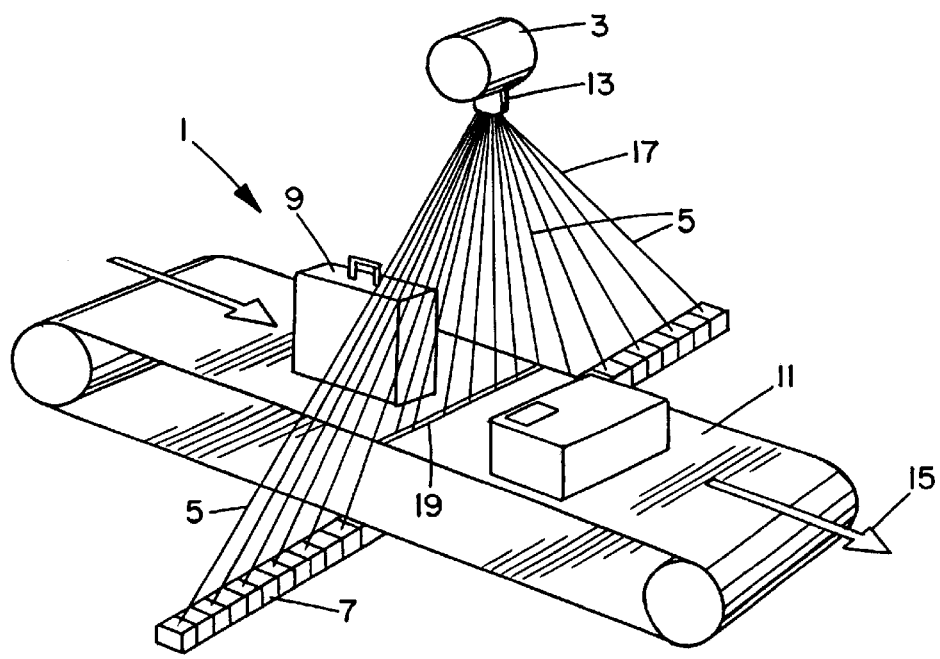
FIG. 1 illustrates the operation of the line scan system of the prior art.

FIG. 1 provides an illustration of the operation of the line scan system 1 of the prior art. An x-ray beam from an x-ray source 3 is passed through a slit collimator 13 to produce a fan beam 17 of x-rays 5 directed substantially perpendicular to the motion 15 along a conveyor belt 11. The fan beam 17 passes through the conveyor belt 11 along a scan line 19. As a target item 9 passes through the fan beam 17, the x-rays that are transmitted through the target item 9, without changing direction, are collected by a multi-element linear array detector 7 to produce a image signal along the scan line 19. The radiant energy that is collected is indicative of the thickness and composition of the material within the fan beam 17. The line scan system 1 identifies material having high atomic number (high Z) since high Z materials readily absorb x-rays 5 to produce a shadow, or an area of low radiant energy, in the resulting image signal. A typical detector 7 is composed of 600–1000 photodiodes covered with a scintillator material.

Figure 2:
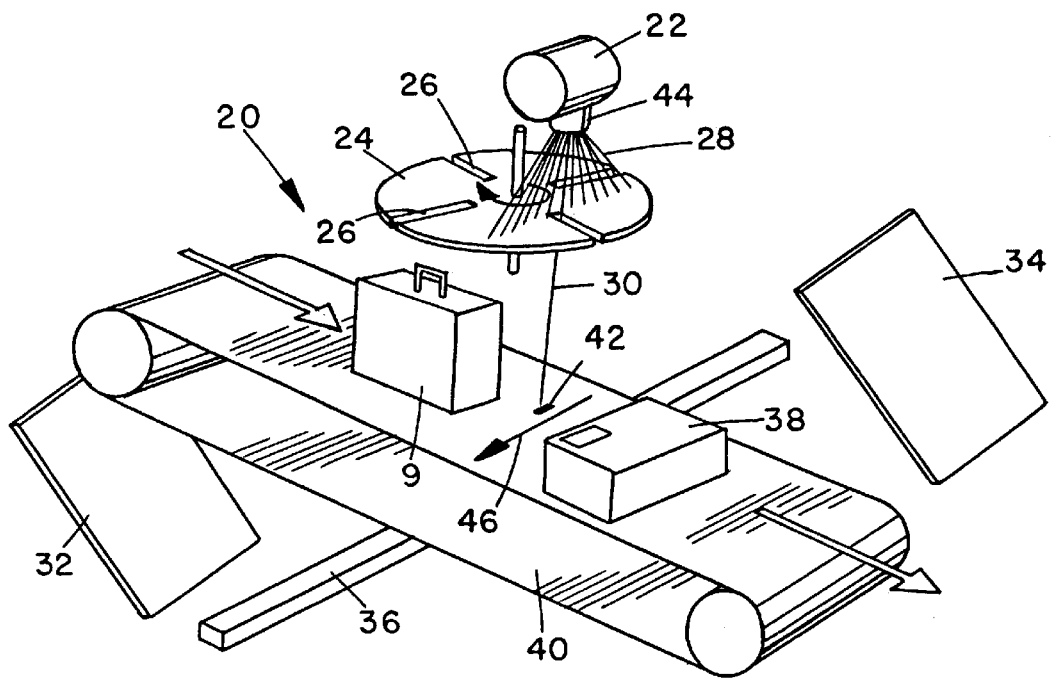
FIG. 2 illustrates the operation of a flying spot system of the prior art.

The operation of the flying spot system 20, an alternate prior art configuration, is shown in FIG. 2. An x-ray beam from an x-ray source 22 is collimated by a slit collimator 44 into a fan beam 28. The fan beam 28 is further collimated into a pencil beam of x-rays 30 that sweeps rapidly across a scan line 46 to impinge upon consecutive small areas 42, or pixels, of the conveyor belt 40 or the target object 9 that intersects the pencil beam 30.

The sweeping pencil beam 30 is produced by positioning a rotating chopper 24 in the path of the fan beam 28. A typical rotating chopper 24 of the flying spot system includes four radial slits 26. Flying spot systems, such as the system disclosed in U.S. Pat. No. 5,181,234 of Smith (the '234 patent), have been utilized in personnel detector systems to detect metals as well as low Z materials that might be concealed beneath a person's clothing.

The transmission x-ray detector 36 of the flying spot system 20 has no spatial resolution because the transmission x-ray detector 36 produces a single signal related to the total number of x-rays striking anywhere along its length, or the single pixel 42 at any given instant in time. Likewise, the back-scatter detectors 32, 34 collect the x-rays scattered from the single pixel 42. Thus, in the flying spot system 20, the spatial resolution along a scan line 46 is determined by the controlled movement of the pencil beam of x-rays 30 produced by the instantaneous positioning of the chopper 24 as it rotates. Each pixel in the acquired back-scatter image corresponds to the small area 42 on the conveyer belt or the target object 9 that is illuminated by the pencil beam of x-rays 30. For example, for an image composed of 800 pixels along the scan line 46, the width of the pencil beam would be nominally 1/800th of the scan line length.

The flying spot system 20, of FIG. 2, has a significant advantage over the line scan system 1 of FIG. 1 because the flying spot system 20 can be used to acquire back-scattered and forward-scattered x-ray images, collectively referred to herein as "back-scatter" unless otherwise indicated. Back-scatter x-rays are scattered or reflected in random directions from the object being scanned, and are therefore not focused. Referring to FIG. 2, the back-scattered x-rays are collected by the back-scatter detector 34, and the forward-scattered x-rays are collected by the forward scatter detector 32. The back-scatter detectors 32, 34 in the flying spot system 20 are simply large area x-ray collectors that do not rely on spatial resolution to form an image. In comparison, the detectors 7 of the line scan system 1 as shown in FIG. 1 inherently rely on the x-rays 5 being focused to form an image, and cannot acquire the unfocused back-scatter images.

The line scan system 1 has certain advantages over the flying spot system 20, including more efficient use of x-ray flux. Referring to FIGS. 1 and 2, the flying spot system 20 only uses a small fraction of the x-rays present in the fan beam 28. In contrast, the line scan system 1 uses the entire fan beam 17. The signal-to-noise ratio of an x-ray image is determined by the number of x-rays used to create the image. Thus, the line scan system 1 has a higher quality image than the flying spot system 20 which sweeps a pencil beam of x-rays 30 across the target object. A common approach to improving the image quality of the flying spot system 20 is to increase the power of the x-ray source 22 to compensate for the inefficient x-ray flux usage. However, an increase in power results in an increase in cost and complexity of the system including an increase in operational costs. For example, increasing the source power may necessitate utilizing rotating-anode x-ray tubes, special electrical wiring to power the system, additional heat dissipation materials, and so on.

Figure 3:
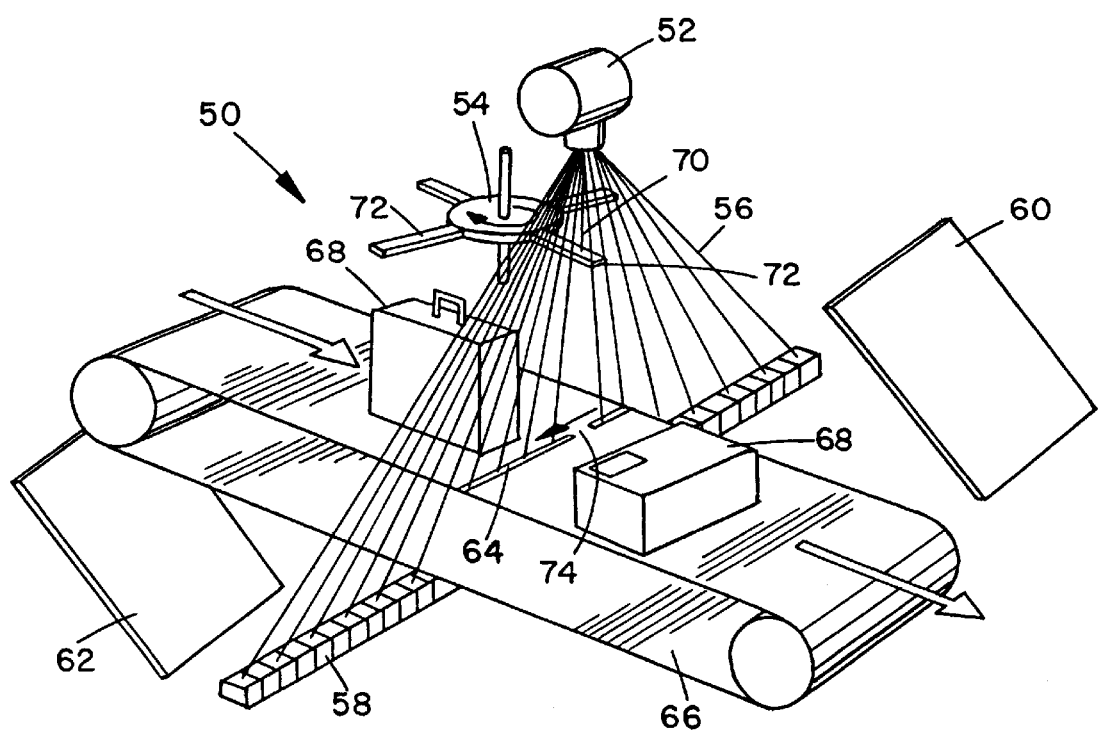
FIG. 3 illustrates an Interrupted-Fan-Beam (IFB) imaging system.

FIG. 3 illustrates the Interrupted-Fan-Beam (IFB) system 50. The IFB system 50 simultaneously acquires both back-scatter images and line scan images to produce an image of the target 68 as it intersects scan line 64. The IFB system 50 thus has the advantages of both the line scan and the flying spot systems of FIGS. 1 and 2, as well as the additional advantages provided by the interrupted fan beam configuration as described further herein. The IFB system 50 operates as a line scan system to acquire transmission images through the use of a fan beam geometry, including an x-ray source and slit collimator 52, and a multi-element detector 58 positioned to accept an incident fan beam 56. Back-scattered x-rays are captured by the back-scatter detectors 60, 62.

The IFB system shown in FIG. 3 is adapted for use with a luggage system that utilizes a conveyor belt. In an alternate embodiment of the present invention the target object 68 is stationary and the fan-beam 56 is moved over the target object 68. For example, an IFB system that sweeps a fan beam across a stationary target object might be necessary for the inspection of large items where the items cannot be placed on a conveyor belt In other embodiments, the object may be moved through the fan beam in a variety of methods. For example, where the IFB system is adapted as a personnel security inspection system to detect objects hidden on a body, following the principles disclosed in the '234 patent, a person might be inspected for concealed objects as he or she walks through an IFB fan beam.

Back-scatter images are produced by the IFB system utilizing an apparatus and method that is, effectively, the "inverse" of the flying spot system. Referring to FIG. 3, x-rays are randomly back-scattered from the target object 68 as it moves on the conveyor belt 66 and through the fan-beam 56. Back-scatter detectors 60, 62 of the preferred embodiment collect the randomly back-scattered x-rays. Other embodiments of the present invention may utilize any number of back-scatter detectors ranging from a single back-scatter detector to an array of back-scatter detectors.

Spatial resolution is provided to produce back-scatter images through the use of a rotating beam-stop 54. The rotating beam-stop 54 is positioned between the x-ray source 52 and the target object 68 for the purpose of interrupting a portion of the fan-beam 56. The beam-stop 54 includes at least one rotating arm 72 having an arm length sufficient to intersect the fan-beam 56 as the arm 72 rotates through the fan-beam 56. In the preferred embodiment of the present invention, the beam-stop includes four arms 72. However, in alternate embodiments, the beam-stop 54 may include any number of arms 72 so long as synchronization of the rotation of the beam-stop 54 with the data acquisition of the transmission detector is possible, as further described below.

In comparison to the flying spot system 20 as shown in FIG. 2 that scans with a pencil beam of x-rays 30, the IFB system 50 of FIG. 3 scans with a pencil beam of "missing" x-rays, or a void 74 in the fan beam. The void 74 in the fan beam is created when an arm 72 of the beam-stop 54 blocks a portion of the rays 70. The width of the blocked area 74 in the fan beam defines the pixel size and controls the spatial resolution along the scan line 64 in the back-scatter image.

In a preferred embodiment, the transmission image contains 600 to 1000 pixels along the scan line 64, while the back-scatter image will only contain 50 to 150 pixels. To prevent the rotating beam-stop 54 from disrupting the transmission image, the beam-stop 54 rotation is synchronized with the data acquisition of the multi-element array 58. In the preferred embodiment of a beam-stop 54 having four arms 72, the beam-stop 54 rotates one quarter turn per each data acquisition period of the multi-element array 58. Since the spatial resolution in the transmission image is controlled by the multi-element array 58, there is no need for the transmission and back-scatter images to have the same pixel size or pixel spacing.

FIGS. 4b and 5b illustrate the differences between the signals of an IFB system 100 of FIG. 5a and the signals in a flying spot scanner 80 of FIG. 4a. The graphs of FIGS. 4b and 5b show typical signals 86, 116 produced for a single scan line or sweep of the fan beams 84, 102 for target objects 92, 112 that fill approximately one-third of the scan line. It should be noted that the graphs of FIGS. 4b, 5b, 6b, and 7b are for illustrative purposes, and are not necessarily accurate in amplitude, resolution, or noise. FIG. 4a of the prior art flying spot system 80 shows a fan beam 84 collimated by a slit collimator 82 that allows successive pencil-beams of x-rays 90 to be transmitted through slit 94. The pencil-beam of x-rays 90 strikes the target object 92, creating back-scattered x-rays along trajectory 96 which are collected by the back-scatter detector 88. As shown in FIG. 4b, the amplitude of signal 86 increases when the pencil beam of x-rays 90 from fan beam 84 sweeps across the target object 92.

In comparison to the prior art as shown in FIGS. 4a and 4b, the IFB signal 116, shown in FIG. 5b, decreases when the "void" in the fan beam sweeps across the target object 112. In the IFB system 100, the entire fan beam 102 less the blocked portion of x-rays 104 is transmitted towards the conveyor belt 114 and target object 112. Thus, any number of x-rays hit the target object and back-scatter along various trajectories 110 and are collected by the back-scatter detectors 108. The total amount of back-scatter produced by the target object 112 when the beam-stop arm 106 is not in the fan beam 102 or aligned with a non-scattering portion of the imaging region is represented in FIG. 5b at a level of 6000 events, i.e. the total number of detected back-scattered x-rays. This level is referred to as the "baseline." The baseline for any particular scan line will depend on the total amount of scattering material appearing anywhere within that scan line. The decrease in the IFB signal 116 represents the decrease in the baseline when the beam-stop arm 106 is aligned anywhere above the scattering object 112 within the scan line. Since the beam-stop arm 106 blocks x-rays, there are fewer x-rays striking the object 112, and thus, less detected scatter.

Figure 6A:
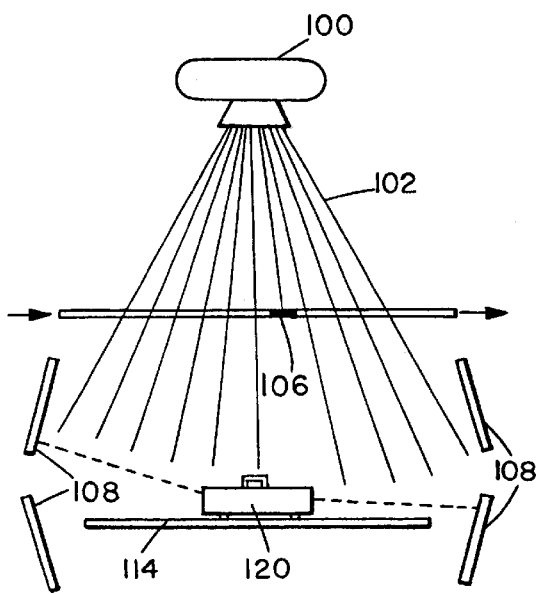
FIG. 6a shows the side view of an IFB imaging system detecting a a thin object.
Figure 7A:
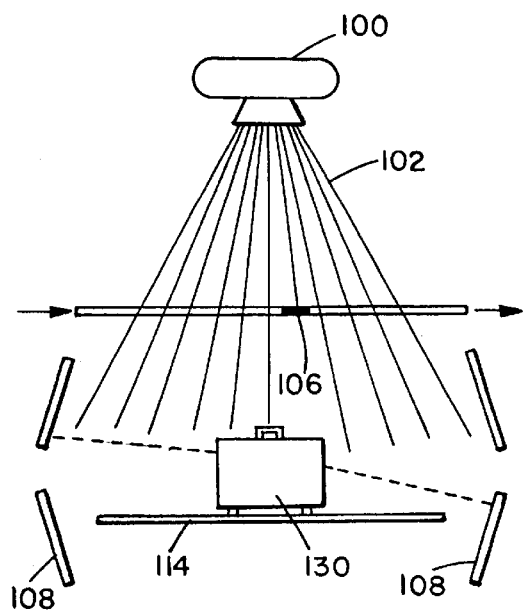
FIG. 7a shows the side view of an IFB imaging system detecting a thick object.
Figure 6B:
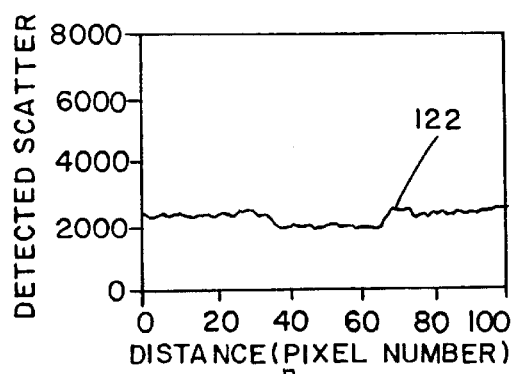
FIG. 6b shows the detected scatter signal and calibrated signal for a thin object.
Figure 6B:
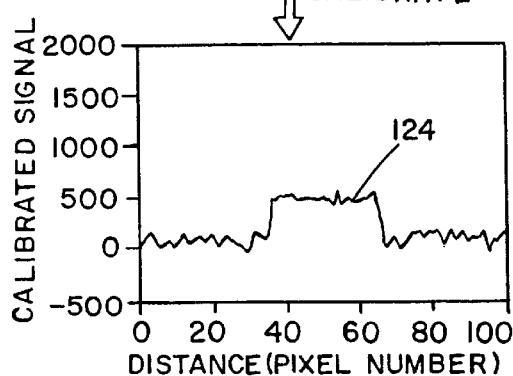
Figure 7B:
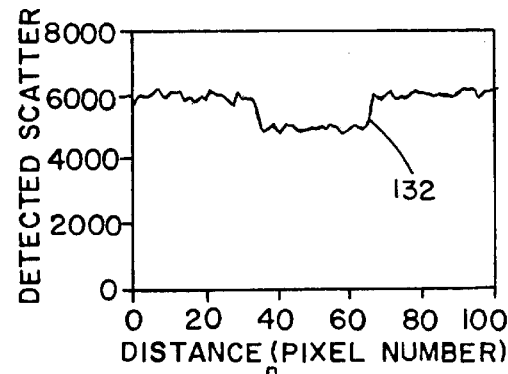
FIG. 7b shows the detected scatter signal and calibrated signal for a thick object.
Figure 7B:
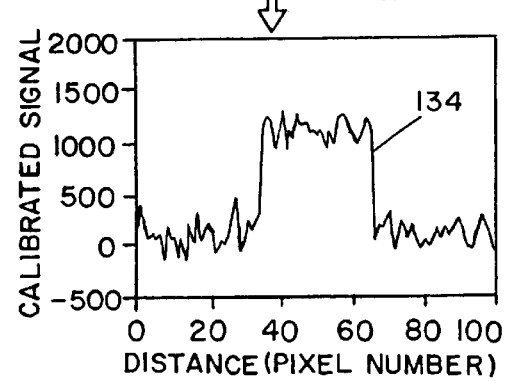

FIGS. 6b and 7b provide an example of how the IFB signals of an IFB system 100 might appear for a thin object 120, shown in FIG. 6a, and a thick object 130, shown in FIG. 7a. The baseline of the thin object signal 122 in FIG. 6b is relatively low and is arbitrarily shown as having a detected scatter level of 2500. A lower baseline is indicative of a thin target object generating little scatter In comparison, the baseline of the thick object signal 132 in FIG. 7b is relatively high at a detected scatter level of 6000 due to the higher level of back scatter from the thicker bag 130.

FIGS. 6b and 7b show that each scan line can be represented as a baseline with depressions due to the presence of objects 120, 130 in the imaging region. Since the baseline changes for each scan line, the signals 122, 132 must be calibrated before they can be used to form an image. Calibration is achieved utilizing an algorithm carried out in a computer system controlling the data acquisition in the IFB system 100. For example, as shown in FIG. 6b, an algorithm may include the steps of subtracting the measured signal 122 from the baseline, a constant value of 2500. The resulting calibrated signal 124 is similar to that produced by the flying spot scanner as shown in FIG. 4b. That is, the amplitude of the signal 124 increases as the thickness of the object 120 increases, and vacant areas of the imaging region correspond to a signal level of zero. Referring to FIGS. 7a and 7b, the calibrated signal 134 shows an increase in the amplitude that corresponds to the thicker object 130.

The transmission image typically has 600 to 1000 pixels per scan line, whereas, the back-scatter image has only 50 to 150 pixels per scan line. The reduction of resolution of the back-scatter image is needed to improve the signal-to-noise ratio as further discussed below. However, since the rotation of the beam-stop and the data acquisition of the transmission detector must be synchronized, the resolution of the two images must be the same in the direction of motion of the conveyer belt. That is, scan lines in both the transmission and back-scatter images have a "width" equal to the distance the conveyer belt moves during a scan line period. A single pixel acquired by the back-scatter system will be highly rectangular, typically 1×4 to 1×20. The vertical and horizontal resolution can be corrected in software to make the final image approximately equal in height and width. In the simplest case, this would involve averaging a certain number of adjacent scan lines, four to twenty scan lines for the above typical rectangular pixels, in the acquired data set to form a single scan line in the displayed image.

Figure 8:
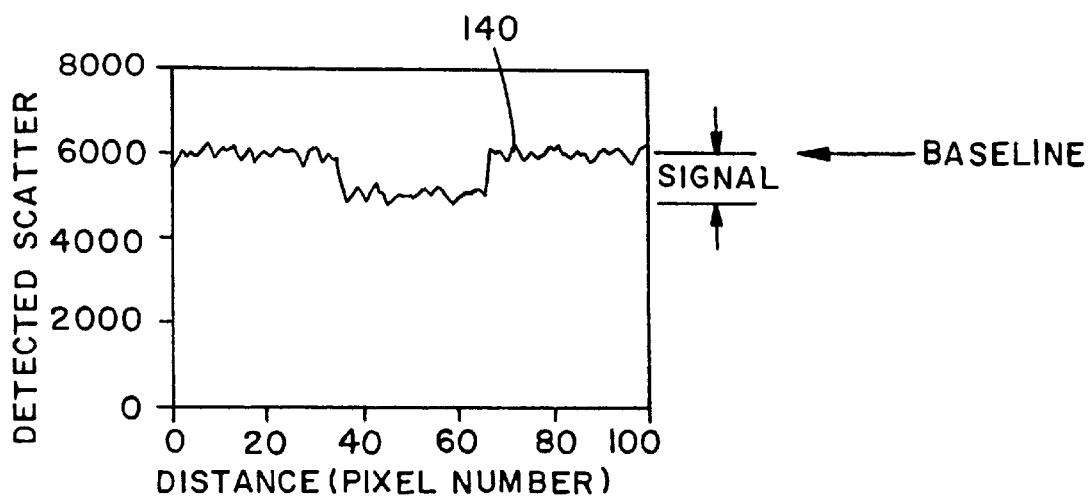
FIG. 8 illustrates the definition of the signal and the baseline for the derivation of the relationship between the signal-to-noise ratio (SNR) and resolution.

FIG. 8 shows a detector signal 140 for a single scan line. The inspection region, i.e., the region within the scan line, contains a thick low-atomic number object, as evidenced by the relatively high detected scatter, that is located in the center one-third of the image. The baseline is the sum of the back-scatter coming from material anywhere on the scan line. As previously discussed, this will change from scan line to scan line. The "signal" is the lowering in the baseline resulting from the beam-stop being aligned with a portion of the target object.

In nearly all x-ray imaging systems, the signal-to-noise ratio (SNR) and the spatial resolution are conflicting parameters, i.e., a trade off exists between generating a high resolution image and the amount of noise present in the image. The following derivation presents the mathematical relationship between resolution and SNR for the Interrupted-Fan-Beam system.

The following are definitions of parameters used in this derivation:

Flux The number of x-rays per pixel in the incident beam of the transmission x-ray system (typical value is 10,000 to 50,000 x-rays)

$P_T$ The number of pixels per scan line in the transmission x-ray system (typical value is 600 to 1000 pixels)

$P_S$ The number of pixels per scan line in the scatter x-ray system (typical value is 50 to 150 pixels)

$S_{TOT}$ A fraction between 0 and 1, indicating the total amount of scatter occurring on a particular scan line. Zero indicates that there is no scattering anywhere along the scan line (i.e. there is nothing in the beam), and 1.0 indicates that the entire length of the scan line is scattering as much as possible (i.e. a thick low-atomic number material across the entire beam). For example, 0.1 would correspond to 10% of the scan line containing a thick low-atomic number material, or that a majority of the scan line has a thin low-atomic material. The typical value is 0.05 to 0.25 for airline baggage.

Eff Scattering efficiency. Fraction of incident x-rays that are detected as scatter when a thick, low-atomic number material is placed in the beam. This depends on both the scattering from the objects and the detector efficiency. A typical value is 0.05 to 0.1.

Baseline The scatter detector output of the number of x-rays per pixel produced by the scatter detectors when the beam-stop is not in the beam or when the beam-stop is aligned with a non-scattering material.

Signal The depression in the baseline of the number of x-rays per pixel caused by the beam-stop being aligned with a scattering object.

Using the above defined parameters, the baseline is defined by equation 1 as follows:

$$\text{Baseline} = \frac{\text{Flux } P_T S_{TOT} \text{ Eff}}{P_S} \quad (1)$$

According to Equation 1, the Baseline is the total number of scattered x-rays detected during a scan line interval divided by the number of pixels during the scan line. Thus, the baseline provides the number of scattered x-rays detected during each pixel.

The Signal is defined as follows:

$$\text{Signal} = \frac{\text{Flux } P_T \text{ Eff}}{P_S^2} \quad (2)$$

The Signal expression is similar to the Baseline expression except for the addition of the $P_S$ term in the denominator and the absence of the $S_{TOT}$ term in the numerator of Equation 2. The added $P_S$ term appears in the denominator of Equation 2 because the beam-stop 106, as shown in FIG. 7a, is blocking the scatter from a single pixel. Thus, the number of x-rays per pixel of the baseline expression is divided by the number of pixels per scan line. Finally, the $S_{TOT}$ term in the numerator of Equation 1 is replaced by "1" in Equation 2 because the pixel being blocked contains a maximum amount of scattering material.

In the Interrupted-Fan-Beam system, the noise is equal to the standard deviation of the baseline signal. Utilizing Poisson statistical methods, the noise is equal to the square root of the baseline. An expression for the signal-to-noise-ratio for a particular scan line (SNRL) is derived as follows:

$$SNR_L = \frac{\text{Signal}}{\text{Noise}} = \frac{\text{Signal}}{\sqrt{\text{Baseline}}} = \frac{\frac{\text{Flux } P_T \text{ Eff}}{P_S^2}}{\sqrt{\frac{\text{Flux } P_T S_{TOT} \text{ Eff}}{P_S}}} \quad (3)$$

Equation 3 reduces to Equation 4 as follows:

$$SNR_L = \frac{1}{P_S^{3/2}} \sqrt{\frac{\text{Flux } P_T \text{ Eff}}{S_{TOT}}} \quad (4)$$

The signal-to-noise ratio of the image must include the effect of averaging adjacent scan lines. For equal resolution in both directions, i.e. parallel and perpendicular to the conveyer motion, the number of scan lines averaged is $P_T/P_S$. The signal-to-noise ratio of the image is derived from the signal-to-noise ratio of the scan line as:

$$SNR = SNR_L \sqrt{\frac{P_T}{P_S}} \quad (5)$$

Combining Equation 4 and Equation 5 results in the following Equation 6:

$$SNR = \frac{P_T}{P_S^2}\sqrt{\frac{\text{Flux Eff}}{S_{TOT}}} \qquad (6)$$

Equation 6 may be expressed in more useful form as follows in Equation 7:

$$SNR = \frac{k}{P_S^2} \text{ where: } k = P_T\sqrt{\frac{\text{Flux Eff}}{S_{TOT}}} \qquad (7)$$

Using Equation 7, the performance of an Interrupted-Fan-Beam system can be calculated based on the known values of the component parameters. Higher values of k correspond to the system having better performance, i.e., a higher signal-to-noise ratio and/or more pixels per scan line. Likewise, lower values of k indicates a lower signal-to-noise ratio and/or fewer pixels per scan line.

Typical line scan x-ray systems operate with flux levels of 10,000 to 50,000 x-rays per pixel, and 600 to 1000 pixels per line. In typical flying-spot systems for luggage inspection, $S_{TOT}$ is in the range of 0.05 to 0.25, while Eff ranges from 0.05 to 0.1. Using the extremes of both ranges, low and high values of k can be calculated for a typical system using the Equation 7 as shown in Table 1.

TABLE 1

| Low value of k | High value of k |
|---|---|
| Flux 10,000 x-ray per pixel | Flux 50,000 x-ray per pixel |
| $P_T$ 600 elements | $P_T$ 1000 elements |
| $S_{TOT}$ 0.25 | $S_{TOT}$ 0.05 |
| Eff 0.05 | Eff 0.1 |
| resulting in: k≈30,000 | resulting in: k≈300,000 |

Figure 9:
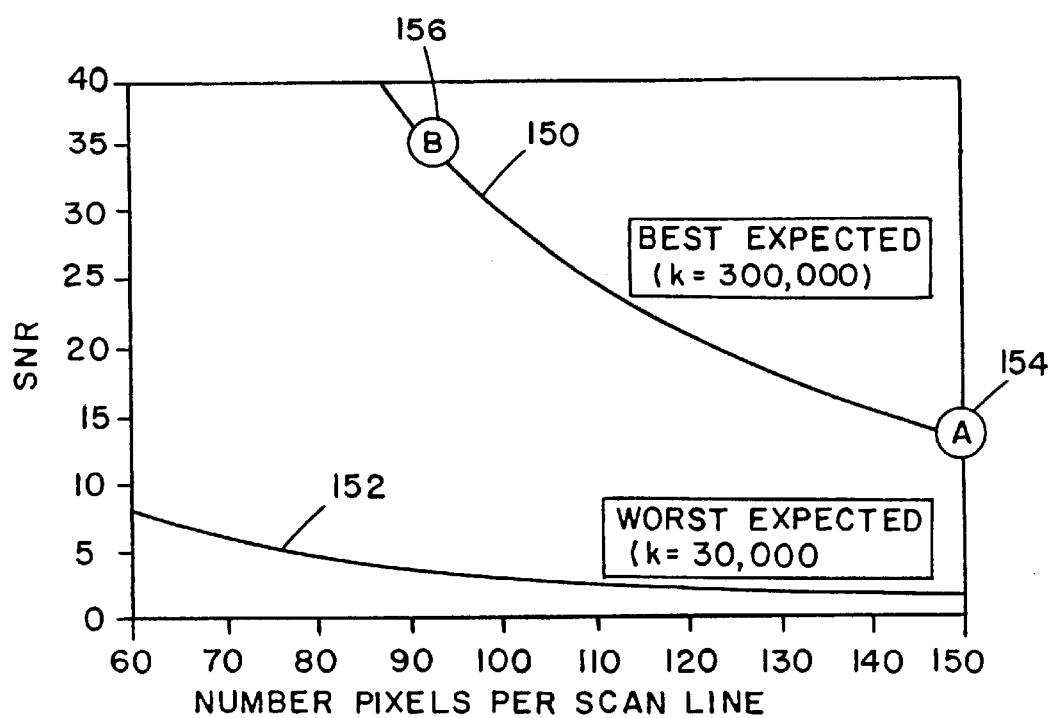
FIG. 9 shows the trade-off between SNR and spatial resolution.

FIG. 9 illustrates the trade-off between signal-to-noise ratio ("SNR") and resolution, or the number of pixels per scan line, within the above reasonably expected high and low values of k. Higher quality images are expected from high values of k. The best expected image quality 150 (k=300,000) and the worst expected image quality 152 (k=30,000), as shown in Table 1, is illustrated in FIG. 9. For example, point "A" 154 shows that a system operating with a high-image quality level, k=300,000, can simultaneously achieve a resolution of 150 pixels per scan line and a signal-to-noise ratio of 13. Point "B" 156 shows that this same system can achieve a signal-to-noise ratio of 35, but at the expense of having the resolution reduced to 93 pixels per scan line. This trade-off between signal-to-noise ratio and resolution is set by the thickness of the arms on the beamstop, and the number of scan lines averaged together.

The Interrupted-Fan-Beam x-ray scanner of the present invention provides a system and method for obtaining back-scatter x-ray images from conventional line scan systems of the prior art. Thus, the advantages of line scan and back-scatter systems, including efficient flux utilization, are realized in addition to the advantages of the IFB system including high resolution low-noise images, The IFB system utilization of both back-scatter and transmission images provides a more thorough security inspection system than is available in prior art systems.

Although a preferred embodiment of the invention has been described above by way of example only, it will be understood by those skilled in the field that modifications may be made to the disclosed embodiment without departing from the scope of the invention, which is defined by the appended claims.

I claim:

1. An imaging system for inspecting a target object, comprising:
   an x-ray source for producing a fan beam of x-rays directed toward the target object along a scan line of a plurality of scan lines;
   a fan beam stop comprising at least one radial arm having an arm width extending from a rotating axis to intersect the fan beam, the radial arm interrupting a portion of the fan beam as the at least one radial arm rotates through the fan beam;
   a transmission x-ray detector positioned in the scan line of the fan beam for producing a transmission signal representative of a portion of the target object intersecting the scan line;
   an inspection surface positioned between the x-ray source and the transmission x-ray detector for moving the target object through the fan beam;
   at least one back-scatter detector positioned within a detection range of the inspection surface for receiving x-rays scattered from the objects and for producing a back-scatter signal representative of the intensity of the x-rays scattered from the objects, wherein the spatial resolution along the scan line is obtained by the radial arm interruption of the fan beam, and wherein each interrupted portion of the fan beam defines a pixel of the back-scatter signal; and
   a processing means for producing a back-scatter image from the back-scatter signal and a transmission image from the transmission signal to produce an image of the objects.

2. The imaging system of claim 1, wherein the rotation of the at least one radial arm is synchronized with a data acquisition cycle of the transmission x-ray detector.

3. The imaging system of claim 1, wherein the at least one radial arm is four radial arms spaced evenly apart.

4. The imaging system of claim 1, wherein each interrupted portion of the fan beam defines a transmission pixel in the transmission signal and wherein each segment of the sequence of segments of pencil beam x-rays defines a back-scatter pixel in the back-scatter signal.

5. The imaging system of claim 4, wherein the back-scatter signal and transmission signal of the object defines a baseline and a detected signal portion.

6. The imaging system of claim 5, wherein the baseline is defined by a baseline equation baseline=(Flux*$P_T$*$S_{TOT}$*Eff), $P_S$;
   wherein the detected signal portion is defined by a detected signal equation detected signal=(Flux*$P_T$*Eff)/$(P_S)^2$;
   wherein the Flux is a number of x-rays per transmission pixel, $P_T$ is a number of transmission pixels per the scan line, $P_S$ is a number of back-scatter pixels per scan line, $S_{TOT}$ is a fraction indicating an amount of scatter occurring during the scan line, and Eff is a scattering detection efficiency.

7. The backscatter imaging system of claim 6, wherein the combined x-ray image has a signal-to-noise ratio (SNR) and a resolution defined by the equations:

SNR=(k)/$(P_S^2)$, wherein k=$P_T$*SQRT((Flux*Eff)/($S_{TOT}$)).

8. The imaging system of claim 1, further comprising a means for moving the fan beam over the target object, and wherein the inspection surface is stationary.

9. The imaging system of claim 1, wherein the back-scatter signal comprises an averaged back-scatter signal obtained by averaging a number of adjacent scan lines of the plurality of scan lines to correct vertical and horizontal resolution of the back-scatter signal.

10. The imaging system of claim 1, wherein the target object is luggage.

11. The imaging system of claim 1, wherein the target object is a shipping container.

12. An x-ray detector system for producing images of target item, the system comprising:
   an x-ray source for producing a fan beam of x-rays, the fan beam of x-rays having a fan beam width;
   a means for passing the target item through the fan beam of x-rays;
   at least one large area x-ray collector positioned proximate to the target item for detecting x-rays scattered from the target item and for producing a back-scatter signal representative of the intensity of the scattered x-rays, the back-scatter signal comprising a baseline portion; and
   a rotating beam-stop positioned between the x-ray source and the transporting means, the rotating beam-stop comprising at least one radial arm for blocking a portion of the fan beam as the at least one radial arm rotates through the fan beam width;
   wherein the rotating beam-stop creates a depression in the baseline portion indicating the presence of the target item.

13. The x-ray detector system of claim 12, further comprising a multi-element detector positioned along the fan beam width for generating a transmission signal of the target items.

14. The x-ray detector system of claim 13, further comprising a processing means for combining the transmission signal and the back-scatter signal into a combined detector image of the target items.

15. A method for scanning a target object to produce an image, comprising the steps of:
   generating a fan-beam of x-rays having a fan-beam width, the fan-beam producing a scan line;
   blocking a sequence of equal portions of the fan-beam across the fan-beam width, each equal portion defining a pixel;
   moving the target object through the fan-beam, the target object intersecting the fan-beam along the scan line;
   collecting back-scatter x-rays that are scattered from the target object;
   generating a backscatter image signal from the collected back-scatter x-rays, comprising the steps of:
   establishing a baseline value representative of the total number of x-rays scattered anywhere along the scan line; and
   indicating a lowering of the baseline value resulting from the blocking of the fan-beam when the pixel is aligned with the target object.

16. The method of claim 15, further comprising the step of:
   outputting a backscatter image from the backscatter image signal.

17. The method of claim 15, further comprising the steps of:
   collecting transmission x-rays transmitted through the target object;
   producing a transmission x-ray signal from the collected transmission x-rays; and
   outputting a transmission image from the transmission x-ray signal.

18. The method of claim 17, further comprising the step of:
   utilizing the transmission x-ray signal and the backscatter image signal in a mathematical relationship to relate a signal-to-noise ratio to a spatial resolution; and
   outputting a final object image utilizing the mathematical relationship.

19. A method for inspecting an object, the method comprising the steps of:
   producing a fan beam of a plurality of x-rays along a scan line during a scanning cycle;
   directing the fan beam towards the object wherein the object absorbs, transmits, or scatters at least some of the plurality of x-rays;
   interrupting sequential portions of the fan beam utilizing a rotating fan beam stop having at least one radial arm, the radial arm having a width for blocking a subset of the plurality of x-rays;
   synchronizing the rotation of the fan beam stop with the scanning cycle;
   collecting the transmitted x-rays of the plurality of x-rays and producing a transmission signal representative of the object during the scanning cycle;
   collecting the back-scattered x-rays of the plurality of x-rays and producing a back-scatter signal representative of the intensity of the x-rays; and
   establishing a spatial resolution of the back-scatter signal based upon the blocked subset of the plurality of x-rays.

* * * * *